United States Patent [19]

Stjernschantz et al.

[11] Patent Number: 5,773,472
[45] Date of Patent: Jun. 30, 1998

[54] METHOD AND MEANS FOR PREVENTION OF CATARACT

[75] Inventors: Johan Stjernschantz; Bahram Resul, both of Upsala, Sweden

[73] Assignee: Pharmacia AB, Upsala, Sweden

[21] Appl. No.: 632,486

[22] PCT Filed: Nov. 3, 1994

[86] PCT No.: PCT/SE94/01035

§ 371 Date: Jun. 4, 1996

§ 102(e) Date: Jun. 4, 1996

[87] PCT Pub. No.: WO95/12401

PCT Pub. Date: May 11, 1995

[30] Foreign Application Priority Data

Nov. 3, 1993 [SE] Sweden .................................. 9303627

[51] Int. Cl.$^6$ .......................... A61K 31/215; A61K 31/19
[52] U.S. Cl. ............................................ 514/530; 514/573

[58] Field of Search ...................................... 514/530, 573, 514/913

[56] References Cited

FOREIGN PATENT DOCUMENTS 0453127  10/1991  European Pat. Off. .
9216199  10/1992  WIPO .

OTHER PUBLICATIONS

Chemical Abstract 117:21186 (1991)—Ueno.

*Primary Examiner*—Zohreh Fay
*Attorney, Agent, or Firm*—Dinsmore & Shohl LLP

[57] ABSTRACT

The present invention is related to the use of thiol-binding prostaglandins or prostaglandin-like substances containing alpha beta unsaturated ketone, esp. Prostaglandins of type A or J and derivatives or analogues thereof, for the preparation of ophthalmically compatible compositions for the prevention of cataracts.

11 Claims, No Drawings

METHOD AND MEANS FOR PREVENTION OF CATARACT

The present invention is related to the use of thiol-binding prostaglandins or prostaglandin-like substances containing alpha beta unsaturated ketone, esp. prostaglandins of type A or J and derivatives or analogues thereof, for the preparation of ophthalmically compatible compositions for prevention of cataract.

Cataract is a general name for opacification of the crystalline lens. There are many causes of cataract and there are several kinds of cataract. Thus cataract may develop due to metabolic diseases such as diabetes mellitus and it may develop due to various kinds of irradiation, e.g. x-ray, ultra-violet and infrared. The most common form of cataract, however, is senile cataract, which can be regarded as a normal physiologic ageing of the lens. Also local diseases and trauma of the eye may cause cataract formation, e.g. chronic iritis and traumatic lesions of the lens. The opacification may be localised to the entire crystalline lens or it may be localised to a certain part of the lens, for example to the nucleus or the cortex, or it may be localised superficially e.g. subcapsularly in the anterior part or the posterior part of the lens. There are also congenital forms of cataract.

Certain drugs may cause cataract as side effect. Such drugs comprise for example corticosteroids, and cholinesterase inhibitors. Presently the only way to treat cataract is operation. Thus, the opacified lens is removed and an artificial intraocular lens is implanted. While such operations usually are successful and restore the vision of the patients, sight-threatening complications may occur. For example sight-threatening endophthalmitis occurs in about 0.1–0.3% of the operations, corresponding to more than 10000 cases per year world-wide. Furthermore, there are several risk factors e.g. glaucoma, diabetes and myopia that may affect the outcome of the surgery negatively. Thus there are patients in whom cataract surgery poses a particular risk and postponement of the operation may be desorable.

While treatment or prevention of cataract has been studied intensely and several drugs have been suggested to revert or halt cataract formation, there is still controversy whether such drugs are effective or not. So far there is no scientific evidence that such drugs have a true therapeutic effect. The formation of large protein aggregates and the relevance of an increase in $T_c$, the highest critical temperature for phase separation, as well as the effect of certain reagents has been studied for instance by Pande et al in Exp Eye Res 57 (1993) 257–264, Pande in Exp Eye Res 681 (Suppl 1) 197 and Truscott et al in Exp Eye Res 49 (1989) 927–940.

We have now unexpectedly found that certain prostaglandins and prostaglandin-like substances, which in the present application are covered by the term "prostaglandins", effectively prevent or retard the formation of cataract in vitro. More specifically such compounds containing an alpha beta unsaturated ketone (enone), and particularly in the cyclopentane ring, have been found effective. The group of prostaglandins comprises particularly prostaglandins of type A and J (for definitions see below) as well as various derivatives and analogues thereof. However, all prostaglandins carry an alpha beta unsaturated ketone in the lower side chain (omega chain) after the first metabolic degradation and could therefore have a similar effect and accordingly be of potential interest, but prostaglandins and prostaglandin analogues with the alpha beta unsaturated ketone in the cyclopentane ring are at present preferred to be used according to the present invention.

The general structure of prostaglandins is illustrated below:

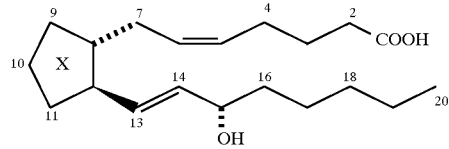

Prostaglandins A, B, C, D, E, F and J contain a cyclopentane ring and two side chains, the upper being the alpha chain and the lower the omega chain. The total number of carbon atoms is 20, the numbering starting from the carboxylic group on the alpha chain. The alpha chain carries a double bond in the cis geometry between carbon atoms 5 and 6, while the omega chain carries a double bond in the trans geometry between carbon atoms 13 and 14. Prostaglandins with 2 double bonds as set out above accordingly, are given the suffix 2. If the 5,6 double bond on the alpha chain is missing the suffix is 1.

Accordingly, the prostaglandins containing 2 double bonds are called $PGA_2$, $PGB_2$, $PGC_2$, $PGD_2$, $PGE_2$, $PGF_{2a}$, $PGJ_2$ while prostaglandins containing 1 double bond are called $PGA_1$, $PGB_1$, $PGC_1$ etc. In addition some prostaglandins may contain a third double bond between carbon atoms 17 and 18, the double bond exhibiting cis configuration. These are called $PGA_3$, $PGB_3$, PGC3, PGD3 etc.

The configuration and the substituents of the cyclopentane ring (X) determine whether the prostaglandin is of the A, B, C, D, E, F or J type. The various configurations of the cyclopentane ring are depicted below:

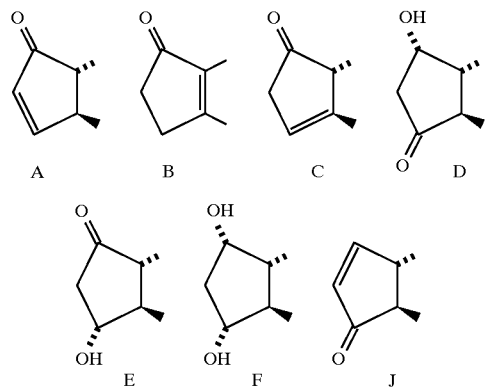

Of these, prostaglandins of A and J type and their derivatives are particularly important since they contain an alpha beta unsaturated ketone in the cyclopentane ring. The alpha beta unsaturated ketone is very reactive forming adducts with thiol groups, such as e.g. sulfhydryl groups on proteins. Accordingly, prostaglandins exhibiting such thiol-binding groups react with the crystallins of the lens to form thiol adducts thereby preventing the sulfhydryl groups from producing disulfide bridges between lens proteins, and thus preventing the proteins from aggregating upon oxidative stress.

In one embodiment of the invention compounds of prostaglandin type, in which the cyclopentane ring contains an alpha beta unsaturated ketone, are utilized. Examples of these type of substances comprises PGA and PGJ in which the sulfhydryl group will be linked to carbon 11 and 9, respectively.

Thus, any derivative of $PGA_{1-3}$, or $PGJ_{1-3}$ having the specific cyclopentane ring configuration, as well as analogous molecules designed to exhibit said functional characteristics can be predicted to be useful in accordance with the present invention. Stabilized prostaglandins of the A or J type, for instance $\Delta^7$-PGA$_2$ and $\Delta^{12}$-PGJ$_2$ are expected to be of importance in this connection.

Certain prostaglandins are known to have pronounced biological effects, for instance in the eye, and several patent applications have been filed covering the use of various derivatives for treatment of glaucoma and ocular hypertension, see for instance EP 093380, WO90/02553 and EP 0344235. Of these, prostaglandins with a ring substituted omega chain, especially those with a phenyl substituent on carbon 17, have been found very potent with no or negligible side effects.

This is most significant because prostaglandins to be used according to the present invention are characterized by having no or only weak biological activity other than the ability to bind to sulfhydryl groups of proteins. The adducts or complexes formed between the prostaglandin compound and the lens proteins should have a rather high formation constant in order to reduce the required dose of active compound as well as the application frequency.

Therefore it is necessary to eliminate from such prostaglandins, e.g. A and J derivatives, any typical side-effects of prostaglandins that may be disadvantageous in the eye, e.g. irritation and conjunctival hyperaemia (redness of the eye), and pigmentation of the iris, as well as biological activities that are desired in other applications, e.g. an intraocular pressure lowering effect.

Accordingly, new prostaglandin A- and J-like molecules can be produced and utilized for prevention of cataract formation.

An important characteristic of prostaglandins of the A and J type are, as discussed above, the alpha beta unsaturated ketone of the cyclopentane ring (X). Additional alpha beta unsaturated ketones can of course be introduced into the omega chain as well as into the alpha chain to give bi- or poly functional molecules with regard to thiol-binding activity.

A prostaglandin derivative or analogue to be used according to the present invention can accordingly be generalised to a structure

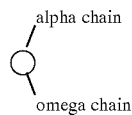

in which the ring is a five to seven-membered ring containing an alpha beta unsaturated ketone, for instance

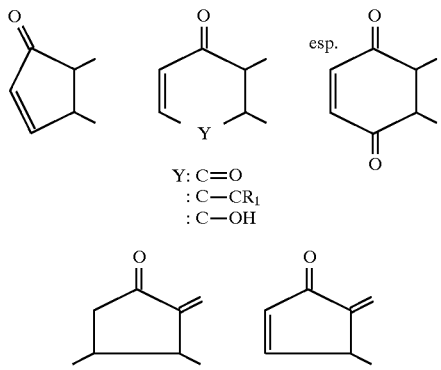

in which the the ring optionally is substitued with one or more lower alkyl groups, e.g with 1–6 carbon atoms, esp 1–4 carbon atoms.

$R_1$ is H or a lower alkyl as defined above.

The alpha chain and the omega chain can have the structure discussed above, in connection with natural prostaglandins, but are in general terms defined as carbon chains Z--R in which Z comprises 4–10 atoms and optionally one or more alpha beta unsaturated ketones. The alpha and omega chains which are equal or different are optionally substitued with one or more alkyl group, esp lower alkyl groups as defined above. R is hydrogen, or an alkyl group, preferably a group with 1–10 carbon atoms, especially with 1–6 atoms, such as 1–4 atoms, or a group C(O)—O—R$_2$ in which R$_2$ is hydrogen or an alkyl group with 1–10 carbon atoms, especially 1–6 atoms, for instance methyl, ethyl, propyl, isopropyl, butyl, isobutyl, neopentyl or benzyl, or a ring structure selected from a group comprising aromatic rings, e.g. phenyl or aromatic heterocyclic groups having 5–6 ring atoms, like thiazol, imidazole, pyrrolidine, thiophene and oxazole, or cycloalkanes or cycloalkenes with 3–7 atoms in the ring, the rings optionally being substituted with alkyl groups as defined above.

The omega chain as well as the alpha chain can optionally be interrupted by preferably not more than one heteroatom O, S or N.

The alpha and omega chains can have the structures given in the general description of prostaglandins above. In preferred embodiments of the invention one or both of the chains contain alpha beta unsaturated ketones as exemplified by the following structures

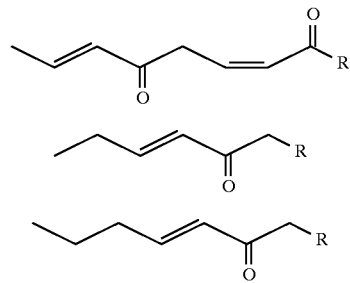

In which R is defined as above.

In order to administer the prostaglandins or their derivatives topically to the eye various lipophilic prodrugs may be employed. Such prodrugs comprise as illustrated by the general formulae given above e.g. esters with 1–10 carbon atoms (for instance alkyl esters), and particularly those with 1–6 carbon atoms. Such esters may comprise e.g. methyl, ethyl, propyl, isopropyl, butyl, isobutyl, neopentyl and benzyl. Hydroxyl groups on the side chains may also be esterified e.g. with pivalolic acid or butyric acid and alike. The group of alternative lipophilic prodrugs includes amides. Depending on the chemical properties of the prostaglandin, salts such as the sodium, chloride or tromethamine salts may be employed.

The compounds may be formulated in physiologically acceptable solutions either aqueous or oil solutions, at a pH range acceptable to the eye. To increase penetration of the compounds into the eye viscosity increasing agents such as hydroxypropyl methylcellulose, polyvinyl alcohol, polyvinyl pyrrolidone, hyaluronic acid and other polymers known for ophthalmic use may be used also in formulations according to the present invention, which also include systems in which the prostaglandin solubilizers and stabilizers like cyclodextrin or analogues thereof have been utilized. Slow release matrices, gels or solid inserts may be used to enhance penetration of the drugs into the eye and to reduce the number of applications necessary. Such formulations containing the active compounds may be preserved with benzalkonium chloride or other preservatives e.g. chlorhexidine, chlorobutanol, parahydroxybenzoic acid and phenylmercuric salts such as nitrate, chloride, acetate and borate and alike, and furthermore may contain additives such as EDTA, EGTA, sorbitol, boric acid etc. and may be packed in multidose dispensers. Alternatively the formulation may be packed in unit dose dispensers whereby the preservative may or may not be excluded from the formulation.

Typically, the new medication for prevention of cataract should be administered topically on the eye at regular intervals 1–4 times daily usually chronically, or intermittently, implying that periods of active treatment are followed by periods without treatment which are followed by periods with active treatment again etc. Depending on the slow-release formulation it may also be possible to administer the drug continuously by replacing the soft or hard ocular drug insert e.g. once a week or once a month or even with longer intervals.

The doses to be used for topical treatment may vary depending on the particular prostaglandin compound and its physical-chemical characteristics. Typically the eye drop composition should contain 0.001–10 mg/ml of the active principle, particularly 0.1–10 mg/ml.

The invention has been exemplified with the following non-limiting examples utilising a relevant in vitro model and with the at present preferred active compound $PGA_2$-tromethamine salt as the new active principle for cataract prevention.

A. Synthesis of $PGA_2$-tromethamine salt.

To a solution of $PGA_2$ (Cayman Chemicals; 30 mg, 0.0897 mmoL) in methanol (3.0 mL), was added tris (hydroxymethy)-aminoethan (10.8 mg; 0.0897 mmoL). The mixture was stirred vigorously at room temperature for 3 h. The solvent was removed in vacuo to give 41 mg of $PGA_2$-tromethamine salt as a light yellow oil.

B. Prevention of cataract formation in vitro

The experiments were performed using bovine lenses. The lenses were removed posteriorly from the eyes usually within 5–6 hours postmortem. The lenses were removed with the capsule and intact as possible and were placed in 15 ml of a phosphate buffer solution, pH 7.5. The lenses were divided into two groups: one group was incubated with prostaglandin $A_2$ tromethamine salt at a final concentration of $10^{-3}$ M in the phosphate buffer, and the other group was incubated in the phosphate buffer only. After 24 hours of incubation in room temperature the lenses were subsided to oxidative stress in 39–40 ° C. with hydrogen peroxide ($H_2O_2$) at a final concentration of 0.2% in the same phosphate buffer, half of the samples containing prostaglandin $A_2$ tromethamine salt and half not. In addition one lens preincubated with $PGA_2$-tromethamine salt and one lens not preincubated with $PGA_2$-tromethamine salt were incubated in the 25 same incubation medium but without $H_2O_2$ and served as negative controls.

Colour photographs were taken at certain intervals for up to 24 hours from the start of incubation with hydrogen peroxide. The vials containing the lenses in the incubation medium were put on a grid pattern drawn on paper, and the degree of cataract was estimated based on how well the grid pattern could be visualized through the lens. A scale from 0 to 3 was used, 0 indicating a totally transparent lens, 1 mild opacification, 2 moderate opacification and 3 full cataract making it practically impossible to visualise the grid pattern through the lens.

The results of the experiments with lenses preincubated with $PGA_2$-tromethamine salt, lenses not preincubated with $PGA_2$-tromethamine salt (positive controls), as well as negative controls are shown in Table I.

TABLE I

| Lens number | Incubation with or without hydrogen peroxide | | | | |
|---|---|---|---|---|---|
| | 0 h | 6 h | 17 h | 21 h | 24 h |
| Lenses incubated with hydrogen peroxide | | | | | |
| Lenses preincubated with $PGA_2$-t. | | | | | |
| A-1 | 0 | 0 | 0 | 0 | 1 |
| A-2 | 0 | 0 | 1 | 2 | 2 |
| A-3 | 0 | 1 | 1 | 1 | 2 |
| Lenses not preincubated with $PGA_2$-t. | | | | | |
| B-1 | 0 | 0 | 2 | 3 | 3 |
| B-2 | 0 | 1 | 2 | 3 | 3 |
| B-3 | 0 | 1 | 2 | 2 | 3 |
| Lenses incubated without hydrogen peroxide | | | | | |
| Lens preincubated with $PGA_2$-t. | | | | | |
| C-1 | 0 | 0 | 0 | 0 | 0 |
| Lens not preincubated with $PGA_2$-t | | | | | |
| C-2 | 0 | 1 | 1 | 1 | 1 |

$PGA_2$-t = prostaglandin $A_2$-tromethamine salt

As can be seen from Table I lenses preincubated with $PGA_2$-tromethamine salt underwent opacification much less and considerably more slowly than the positive control lenses not preincubated with $PGA_2$-tromethamine salt. Lenses not subsided to hydrogen peroxide challenge at all (C-1 and C-2) showed no or only slight opacification, demonstrating that the incubation for 24 hours in 39–40 ° C. had no or only a small effect on the transparency of the lenses.

These experiments confirm that the $PGA_2$ protects the lens from oxidative damage even when such a marked oxidation is used as 0.2% hydrogen peroxide solution in 39–40 ° C. In the clinical situation the degree of oxidative stress on the crystalline lens is only a fraction of that used in the present experiments, and cataract usually develops during years or decades. Therefore much smaller amounts of the active principle can be anticipated to have a protective effect against oxidative and other damage of the lens making it possible to administer the drug topically to the eye cronically or at certain intervals.

We claim:

1. A method of preventing cataract by administering to the eye a composition comprising a prostaglandin and an ophthalmically compatible carrier, in an amount effective to prevent cataract, the prostaglandin being a compound of formula (I)

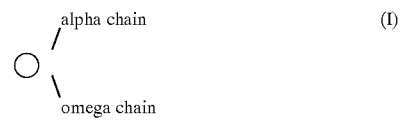

wherein
   ○ is a ring having 5 to 7 members and containing an alpha beta unsaturated ketone, optionally being substituted with one or more alkyl groups of 1 to 6 carbon atoms, and each of alpha chain and omega chain is individually of the formula Z-R wherein Z is a carbon chain of 4 to 10 carbon atoms, optionally including a heteroatom selected from the group consisting of O, S and N, and R is selected from the group consisting of hydrogen, an alkyl group of 1 to 10 carbon atoms, C(O)—O—$R_2$ in which $R_2$ is hydrogen or an alkyl group of 1 to 10 carbon atoms, and ring structures selected from the group consisting of phenyl, aromatic heterocyclic groups having 5 to 6 ring atoms, and cycloalkyl and cycloalkene groups having 3 to 7 ring atoms, the ring structures optionally being substituted with one or more alkyl groups of 1 to 10 carbon atoms, or an ester, amide or salt of a compound of formula (I).

2. A method according to claim 1, wherein the composition comprises the ester, amide or salt of a compound of formula (I).

3. A method according to claim 1, wherein the composition comprises a $C_1$–$C_{10}$ ester of a compound of formula (I).

4. A method according to claim 1, wherein the composition comprises 0.001–10 mg/ml of the prostaglandin.

5. A method according to claim 1, wherein the composition comprises 0.1–10 mg/ml of the prostaglandin.

6. A method according to claim 1, wherein the prostaglandin comprises a PGA or a PGJ, or an ester, amide or salt thereof.

7. A method according to claim 1, wherein the prostaglandin comprises a $PGA_2$ or a $PGJ_2$, or an ester, amide or salt thereof.

8. A method according to claim 1, wherein the composition is topically applied.

9. A method of preventing cataract by administering to the eye a composition comprising a prostaglandin and an opthalmically compatible carrier, in an amount effective to prevent cataract, the prostagiandin comprising a PGA or a PGJ, or an ester, amide or salt thereof.

10. A method according to claim 9, wherein the composition comprises 0.001–10 mg/ml of the prostaglandin.

11. A method according to claim 9, wherein the composition comprises 0. 1–10 mg/ml of the prostaglandin.

* * * * *